United States Patent
Bartels

(10) Patent No.: US 6,805,875 B2
(45) Date of Patent: Oct. 19, 2004

(54) COMPOSITION AND METHOD FOR TREATING DIAPER RASHES AND SKIN IRRITATIONS CAUSED BY ACIDIC SECRETIONS

(75) Inventor: Jennifer F. Bartels, 601 N. Hazel St., Hammond, LA (US) 70401

(73) Assignee: Jennifer F. Bartels, Hammond, LA (US)

( * ) Notice: Subject to any disclaimer, the term of this patent is extended or adjusted under 35 U.S.C. 154(b) by 32 days.

(21) Appl. No.: 10/368,716

(22) Filed: Feb. 18, 2003

(65) Prior Publication Data

US 2003/0157195 A1 Aug. 21, 2003

Related U.S. Application Data

(60) Provisional application No. 60/358,329, filed on Feb. 19, 2002.

(51) Int. Cl.[7] .............................. A61K 7/00; A61K 9/70; A61K 33/10; A61K 33/08
(52) U.S. Cl. ....................... 424/401; 424/443; 424/686; 424/690; 424/692; 514/865
(58) Field of Search ................................ 424/401, 443, 424/686, 690, 692; 514/865

(56) References Cited

U.S. PATENT DOCUMENTS

| 4,764,505 A | * | 8/1988 | Fujinuma et al. ............. 514/35 |
| 5,362,488 A | * | 11/1994 | Sibley et al. ............ 424/78.05 |
| 5,618,529 A | * | 4/1997 | Pichierri .................. 424/78.06 |
| 5,652,274 A | * | 7/1997 | Martin ....................... 514/724 |
| 5,762,945 A | * | 6/1998 | Ashley ....................... 424/401 |
| 5,972,321 A | * | 10/1999 | Kligerman et al. ........... 424/65 |
| 6,066,673 A | * | 5/2000 | McIver et al. .............. 514/634 |
| 6,296,862 B1 | * | 10/2001 | Paul et al. .................. 424/402 |
| 6,506,392 B2 | * | 1/2003 | Siamon ...................... 424/401 |
| 2002/0136755 A1 | * | 9/2002 | Tyrell et al. ................ 424/443 |

FOREIGN PATENT DOCUMENTS

BR    8702742 A   * 12/1987

* cited by examiner

Primary Examiner—Thurman K. Page
Assistant Examiner—Marina Lamm
(74) Attorney, Agent, or Firm—Nath & Associates; Todd Juneau; Joshua Goldberg

(57) ABSTRACT

A topical composition and method for the treatment of the symptoms of diaper rashes and skin irritations caused by acidic secretions comprising a) a pH-raising ingredient selected from the group consisting of sodium hydrogen carbonate (bicarbonate of soda), magnesium hydroxide, calcium carbonate, aluminum hydroxide, and mixtures thereof; b) an anhydrous base ointment; c) polysorbate 80; d) a pharmaceutically acceptable diluent; and e) butylated hydroxy toluene, wherein said pharmaceutically acceptable diluent is purified water. The pH of the topical composition is adjusted by adding droplets of glacial acetic acid. The composition can also further comprise AQUAPHOR™. Embodiments disclosed include a cream, dusting powder, spray, bath soak and effervescent tablet, and also the application of the lotion composition to a bodyside diaper liner.

5 Claims, No Drawings

COMPOSITION AND METHOD FOR TREATING DIAPER RASHES AND SKIN IRRITATIONS CAUSED BY ACIDIC SECRETIONS

This application claims the benefit of U.S. Provisional Application No. 60/358,329, filed Feb. 19, 2002.

BACKGROUND OF THE INVENTION

The present invention relates generally to topical compositions and treatments of a skin condition commonly known as "diaper rash" and more particularly, acidic-type diaper rash and other skin irritations caused by acidic bodily secretions, usually resulting from teething, antibiotic dosages, bacterial infections, and an acidic diet.

A skin condition commonly known as diaper rash is prevalent among infants everywhere. This invention focuses on a specific type of diaper rash and skin irritation, the type associated with acidic bodily secretions generated by teething, antibiotic dosages, bacterial infections, and an acidic diet.

A prior art reference was found in U.S. Pat. No. 5,972,321 issued to Kligerman, which discusses a compound, calcium glycerophosphate, which potentially is a remedy for acidic diaper rashes, although the claims section of said prior art omits the acidic diaper rash discussion. The present invention solves the acidic rash symptoms without the use of calcium glycerophosphate. Calcium glycerophosphate is not necessary to treat the symptoms of infant acidic diaper rash. Moreover, calcium glycerophosphate was developed and is being marketed as a food additive for reducing acid in the digestive tract. The present invention was specifically formulated for the treatment of acidic diaper rash, taking into account all factors necessary to make said treatment effective and safe.

Another prior art reference was found in U.S. Pat. No. 6,506,392 issued to Siamon which lists ingredients including sodium bicarbonate, sodium carbonate, and tisodium phosphate. The prior art does not address the present invention's goals of adjusting the pH of the skin. Moreover, some members of the class of alkali metals that the composition is comprised of is disclosed in the patent document to be harmful to the user if used internally or ingested, making this prior art composition unsuitable for infant skincare and diapering use. Furthermore, the percentages of the acid trisodium phosphate in U.S. Pat. No. 6,506,392 issued to Siamon does not fulfill the goals of the present invention, which is to raise the pH of the solution, not lower it.

Prior art related to diaper rash occasionally addresses buffered skin creams which attempt to stabilize pH as in U.S. Pat. No. 5,362,488 issued to Sibley and U.S. Pat. No. 5,436,007 issued to Hartung. This prior art establishes a desired pH range for said cream in a range of 4.5–6.0.

The present invention's active ingredients more closely resemble antacid formulations for the digestive tract as in U.S. Pat. No. 5,914,135 issued to Dubek and in U.S. Pat. No. 6,066,342 issued to Gurol. However, the present invention and its uniquely formulated composition is exclusively related to alleviating diaper rash and skin irritations caused by acidic secretions.

Other prior art related to diaper rash as in U.S. Pat. No. 5,091,193 issued to Enjolias and U.S. Pat. Nos. 5,618,529 and 5,194,261 issued to Pichierri disclose a barrier type cream in which the stated purpose is to protect the infant's skin from moisture resulting from bodily secretions, or an antibacterial element such as Nystatin, as in U.S. Pat. No. 5,762,945 issued to Ashley which prevents the growth of bacteria which contributes to infant diaper rash.

Consequently, a need has been felt for providing a composition and method for treating acidic diaper rash which can raise the pH of the skin sufficient to eliminate redness and irritation, yet gentle enough for an infant's delicate skin.

Moreover, the present invention is unique and innovative due to its composition and method and its difference in approach to the prior art in solving the problem of diaper rash and skin irritations caused by acidic secretions.

SUMMARY OF THE INVENTION

It is therefore an object of the present invention to provide an innovative and effective composition and method for treating acidic-type diaper rashes and skin irritations.

It is yet another object of the present invention to provide another formulation and method besides barrier creams to treat acidic type diaper rash and skin irritations by effectively raising the pH of the skin, thus offsetting the acid burn which results from gastric imbalances caused by teething, antibiotic dosages, bacterial infections, and/or an acidic diet.

It is a feature of the present invention to provide a novel use for the formulation in the form of a cream, lotion, spray, dusting powder, bath salts and/or effervescent molded tablet, and/or a composition for a disposable diaper's interior liner, all of which increase the pH of the skin to the degree that redness and irritation is alleviated.

Advantages of the present invention are that it is easily applied, the ingredients are readily available and inexpensive to manufacture, the active ingredients have been proven to be safe over years of uses in other applications (i.e., the digestive tract), and the composition is effective by itself or in combination with other conventional treatments.

DESCRIPTION OF THE PREFERRED EMBODIMENTS

It has now been discovered, a topical composition of a combination of pH-raising ingredients such as sodium hydrogen carbonate (bicarbonate of soda), magnesium hydroxide, calcium carbonate, aluminum hydroxide and mixtures thereof. This active ingredient(s) would function in a preparation of an anhydrous base ointment, polysorbate 80, a pharmaceutically acceptable diluent, and butylated hydroxy toluene. pH is adjusted with the addition of glacial acetic acid. The high pH ingredients sodium hydrogen carbonate and/or magnesium hydroxide, calcium carbonate, and/or aluminum hydroxide could also be combined with AQUAPHOR™ Beiersdorf to yield a similar composition. This composition can provide relief from the symptoms of diaper rash or skin irritations caused by acidic secretions resulting from teething, antibiotic dosages, bacterial infections, and/or an acidic diet.

EXAMPLE 1

In its preferred embodiment, the composition is made of the following ingredients:

a. 0.5–60% sodium hydrogen carbonate (bicarbonate of soda)
b. 0–60% magnesium hydroxide
c. 0–60% calcium carbonate
d. 0–5% aluminum hydroxide
e. 5–95% anhydrous base ointment
f. 1–15% polysorbate 80
g. 10–85% pharmaceutically acceptable diluent h. 0.001–10% butylated hydroxy toluene (BHT)

i. 0–0.5% acetic acid to adjust pH wherein said pharmaceutically acceptable diluent is purified water.

EXAMPLE 2

In a particularly preferred embodiment, the composition is made of the following ingredients:

a. 7 grams sodium hydrogen carbonate (bicarbonate of soda)

b. 40 grams anhydrous ointment base c. 2 grams polysorbate 80 d. 50 grams purified water e. 200 milligrams butylated hydroxy toluene

It is also currently envisioned that for the cream, lotion, spray, dusting powder, bath salts and/or effervescent molded tablet, and/or a composition for the interior liner of a disposable diaper or absorbent article, that inert carriers, fillers, or other inactive ingredients may be included to vary the effective concentration of the active ingredients depending on the application. The pH-raising ingredients sodium hydrogen carbonate and/or magnesium hydroxide, calcium carbonate, and/or aluminum hydroxide could also be combined with AQUAPHOR™ Beiersdorf to yield a similar composition. Also, the composition can include the addition of fragrance and/or color to provide a more pleasant sensory experience for the caregiver and infant.

The present invention is a treatment and composition which establishes a pH range of 7.0–10.4 in combination with the high pH particles of the active ingredients having contact with the skin to give fast relief to the condition of acidic diaper rash due to teething antibiotic dosages, bacterial infections, and/or an acidic diet. Moreover, present invention does not purport or attempt to be a barrier cream, but a therapeutic treatment to reverse the effects of highly acidic secretions on the skin.

The foregoing description is included to illustrate the operation of the preferred embodiment and is not meant to limit the scope of the invention. From the foregoing description, many variations will be apparent to those skilled in the art that would yet be encompassed by the spirit and scope of the invention.

What is claimed is:

1. A composition for topically treating diaper rash and other skin irritations caused by acidic secretions consisting of a) a pH-raising ingredient selected from the group consisting of sodium hydrogen carbonate (bicarbonate of soda), magnesium hydroxide, calcium carbonate, aluminum hydroxide, and mixtures thereof; b) an anhydrous base ointment; c) polysorbate 80; d) a pharmaceutically acceptable diluent; e) butylated hydroxy toluene and f) optionally, fragrance and/or color, wherein said pharmaceutically acceptable diluent is purified water and wherein pH of the composition is adjusted to 7.0–10.4 with glacial acetic acid.

2. A composition for topically treating diaper rash and skin irritations caused by acidic secretions consisting of:

a. 0.5–60% sodium hydrogen carbonate (bicarbonate of soda)

b. 0–60% magnesium hydroxide

C. 0–60% calcium carbonate d. 0–5% aluminum hydroxide e. 5–95% anhydrous base ointment f. 1–15% polysorbate 80 g. 10–85% pharmaceutically acceptable diluent h. 0.001–10% butylated hydroxy toluene (BHT)

i. 0–0.5% acetic acid to adjust pH, wherein said pharmaceutically acceptable diluent is purified water.

3. The composition of claim 1, wherein said composition is applied to an absorbent article to maintain skin health.

4. The composition of claim 3, wherein said absorbent article is a diaper.

5. A method for treating diaper rash and skin irritations caused by acidic secretions in a patient, comprising topically applying to the patient a composition consisting of a) a pH-raising ingredient selected from the group consisting of sodium hydrogen carbonate (bicarbonate of soda), magnesium hydroxide, calcium carbonate, aluminum hydroxide, and mixtures thereof; b) an anhydrous base ointment; c)polysorbate 80; d) a pharmaceutically acceptable diluent; e) butylated hydroxy toluene; and f) optionally, fragrance and/or color, wherein said pharmaceutically acceptable diluent is purified water and wherein pH of the composition is adjusted to 7.0–10.4 with glacial acetic acid.

* * * * *